Figure 1:
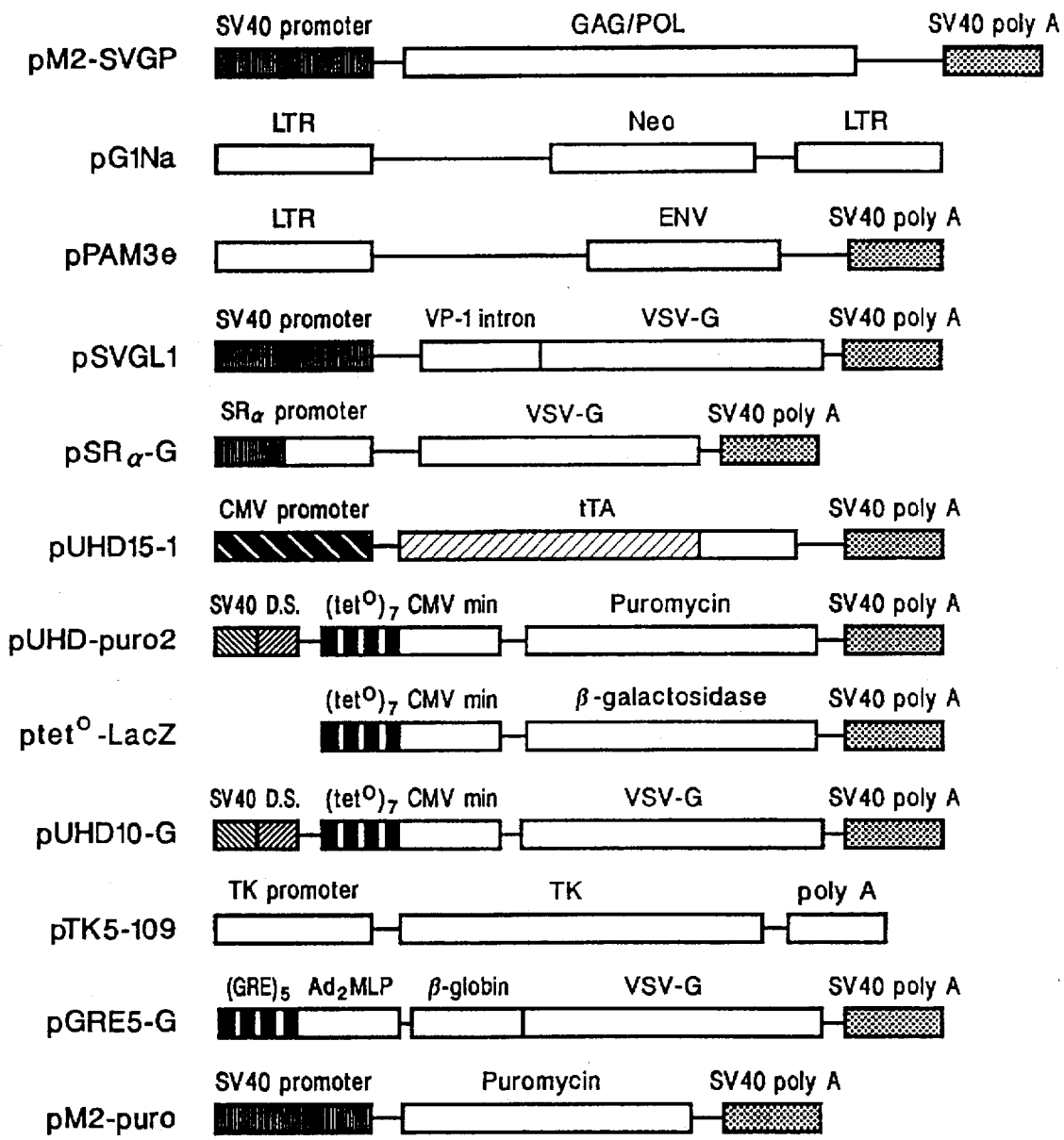

United States Patent [19]
Yang et al.

[11] Patent Number: 5,750,396
[45] Date of Patent: May 12, 1998

[54] STABLE VIRUS PACKAGING CELL LINES

[75] Inventors: Yanping Yang; Elio F. Vanin; Gerard C. Grosveld; Arthur W. Nienhuis, all of Memphis, Tenn.

[73] Assignees: St. Judes Children's Research Hospital, Memphis, Tenn.; Genetic Therapy, Inc., Gaithersburg, Md.

[21] Appl. No.: 437,188

[22] Filed: May 8, 1995

[51] Int. Cl.$^6$ .................. C12N 5/10; C12N 5/08
[52] U.S. Cl. .............. 435/357; 435/366; 435/320.1; 536/23.72; 536/24.1
[58] Field of Search ............... 435/69.1, 172.1, 435/172.3, 240.2, 320.1, 325, 371, 353, 354, 357, 363, 366; 536/23.1, 23.72, 24.1

[56] References Cited

FOREIGN PATENT DOCUMENTS

| | | |
|---|---|---|
| 0440219 | 8/1991 | European Pat. Off. . |
| WO 92/14829 | 9/1992 | WIPO . |
| WO 94/29440 | 12/1994 | WIPO . |
| WO 94/29442 | 12/1994 | WIPO . |

OTHER PUBLICATIONS

Gossen, M. et al., "Tight control of gene expression in mammalian cells by tetracycline–responsive promoters," *Proc. Natl. Acad. Sci. USA* 89: 5547–5551 Jun. (1992).

Yang, Y. et al., "Vesicular Stomatitis Virus (VSV) Pseudotyped Murine Retrovirus Mediates Gene Transfer Into Human Hematopoietic Cells " *Blood* 84(10); Suupl. I:358a Dec. (1994) Abstract No. 1417.

Yee, J. et al., "A general method for the generation of high–titer, pantropic retroviral vectors: Highly efficient infection of primary hepatocytes," *Proc. Natl. Acad. Sci. USA* 91:9564–9568 Sep. (1994).

*Primary Examiner*—David Guzo
*Attorney, Agent, or Firm*—Sterne, Kessler, Goldstein & Fox P.L.L.C.

[57] ABSTRACT

The field of the invention is recombinant packaging and producer cell lines for producing infectious retroviral vectors. The invention more specifically relates to the generation of pseudotyped retroviral vectors with a broad host range which can be produced at high titers in specially constructed packaging cell lines. Most specifically, the invention relates to the generation of pseudotyped retroviral vectors having vesicular stomatitis virus-G protein (VSV-G) as the membrane-associated viral envelope protein.

27 Claims, 7 Drawing Sheets

STABLE VIRUS PACKAGING CELL LINES

BACKGROUND OF THE INVENTION

1. Field of the Invention

The field of the invention is recombinant packaging and producer cell lines for producing infectious retroviral vectors. The invention more specifically relates to the generation of pseudotyped retroviral vectors with a broad host range which can be produced at high titers in specially constructed packaging cell lines. Most specifically, the invention relates to the generation of pseudotyped retroviral vectors having vesicular stomatitis virus-G protein (VSV-G) as the membrane-associated viral envelope protein.

2. Description of the Background Art

The ability to transfer exogenous genes into human somatic cells and achieve expression of the transferred gene at levels that are of therapeutic value would create many opportunities for human gene therapy. Hematopoietic stem cells, lymphocytes, vascular endothelial cells, respiratory epithelial cells, keratinocytes, skeletal and cardiac muscle cells, neurons and cancer cells are among the proposed targets for therapeutic gene transfer, either ex vivo or in vivo (Miller, A. D., *Nature (London)* 357:455–460 (1992); Miller, A. D., *Curr. Top. Microbiol. Immunol.* 158:1–24 (1992); Nienhuis, A. W. et al., "Viruses in therapeutic gene transfer vectors," in *Viruses and Bone Marrow*, N. S. Young, ed., Dekker, New York, N.Y. (1993), pp. 353–414; Mulligan, R. C., *Science* 260:926–932 (1993)).

Many proposed gene therapy applications include the use of viral vectors in an effort to capitalize on the ability of these naturally infectious agents to efficiently transfer and express genes in susceptible target cells. Among the various vector systems that have been developed are those based on murine leukemia viruses (MuLV) (Miller, A. D., *Curr. Top. Microbiol. Immunol.* 158:1–24 (1992)), adenovirus (Nienhuis, A. W. et al., "Viruses in therapeutic gene transfer vectors," in *Viruses and Bone Marrow*, N. S. Young, ed., Dekker, New York, N.Y. (1993), pp. 353–414), adeno-associated virus (Muzyczka, N., *Curr. Top. Microbiol. Immunol.* 158:97–129 (1992); Muzyczka, N., *J. Clin. Invest.* 94:1351 (1994)), Herpes simplex virus (Glorioso, J. C. et al., *Ann. Neurol.* 35 (suppl.):S28-34 (1994)), and various lentiviruses including human immunodeficiency virus (HIV) (Pozansky, M. et al., *J. Virol.* 65:532–536 (1991); Shimada, T. et al., *J. Clin. Invest.* 88:1043–1047 (1991)). Each has potential advantages for specific applications and various biological and technical limitations that must be overcome to allow widespread and effective clinical use.

Retroviral vectors have been used to transfer genes efficiently by exploiting the viral infectious process. Foreign genes cloned into the retroviral genome can be delivered efficiently to cells susceptible to infection by the retrovirus. Through other genetic manipulations, the replicative capacity of the retroviral genome can be destroyed. Such altered vectors can introduce new genetic material to a cell but are unable to replicate. A helper virus or a packaging system can be used to permit vector particle assembly and exit from the packaging cell. Such vector particles can mediate the transfer of genes into the cells they infect.

The development of retroviral vector systems, based on components of the murine leukemia virus (MuLV) genome, is the most advanced, and indeed many current human gene therapy protocols involve the use of such vectors (Miller, A. D., *Nature (London)* 357:455–460 (1992); Miller, A. D., *Curr. Top. Microbiol. Immunol.* 158:1–24 (1992); Nienhuis, A. W. et al., "Viruses in therapeutic gene transfer vectors," in *Viruses and Bone Marrow*, N. S. Young, ed., Dekker, New York, N.Y. (1993), pp. 353–414). Among the advantages of retroviral vectors are their ability to efficiently integrate an unrearranged proviral genome into proliferating target cells. Limitations include the relatively restricted host range, based in part on the level of expression of the membrane protein that serves as a viral receptor (Kavanaugh, M. P. et al., *Proc. Natl. Acad. Sci. (USA)* 91:7071–7075 (1994)). Other limitations are the inability to integrate in non-dividing cells (Springett, G. M. et al., *J. Virol.* 63:3865–3869 (1989); Miller, D. G. et al., *Mol. Cell. Biol.* 10:4239–4242 (1990); Roe, T. et al., *EMBO J.* 12:2099–2108 (1993)), modest vector titers available with current packaging systems and fragility of vector particles that precludes purification and concentration.

It is possible to alter the host range of cells that retroviral vectors can infect by including an envelope gene from another closely-related virus. Thus, one strategy that has been proposed for expanding the host range of retroviral vectors is to take advantage of the capacity of the envelope proteins of certain viruses to participate in the encapsidation of the genome and matrix components of other viruses. Miller et al. (*Mol. Cell. Biol.* 5:431–437 (1985)) constructed a Moloney MuLV (MoMuLV)-derived vector to introduce a selectable marker, dihydrofolate reductase, into susceptible cells, and included the envelope region from the related amphotropic retrovirus 4070A to broaden the host range of the vector. Other investigators have described pseudotypes of retroviral vectors whose host cell range has been altered by substitution of envelope proteins from different viruses. Substitution of the Gibbon ape leukemia virus envelope protein for the amphotropic retroviral envelope has resulted in vectors capable of infecting bovine and hamster cells, species not susceptible to infection with retroviral vectors containing the MoMuLV envelope protein (Miller et al., *J. Virol.* 65:2220–2224 (1991)). Further, substitution of the HTLV-1 envelope protein has been shown to restrict the host range of an MoMuLV-based vector to cells infectible by HTLV-1 (Wilson, C. et al., *J. Virol.* 63:2374–2378 (1989). See also Zavada, J., *J. Gen. Virol.* 15:183–191 (1972); Weiss, R. A. et al., *Virology* 76:808–825 (1977)). Such pseudotyped virions exhibit the host range and other properties of the virus from which the envelope protein is derived.

The G protein of vesicular stomatitis virus (VSV-G) (Rose & Gallione, *J. Virol.* 39:519–528 (1981); Rose & Bergmann, *Cell* 30:753–762 (1982)) efficiently forms pseudotyped virions with genome and matrix components derived from MuLV (Emi, N. et al., *J. Virol.* 65:1202–1207 (1991); Burns, J. C. et al., *Proc. Natl. Acad. Sci. (USA)* 90:8033–8037 (1993); Yee, J. K. et al., *Proc. Natl. Acad. Sci (USA)* 91:9564–9568 (1994)). These VSV-G pseudotyped vectors have a very broad host range and can be concentrated to titers of greater than $10^9$/ml by ultracentrifugation. Vector particles containing VSV-G as the only envelope protein are formed efficiently; their ability to infect cells is blocked by neutralizing anti-VSV antibodies (Emi, N. et al., *J. Virol.* 65:1202–1207 (1991); Yee, J. K. et al., *Proc. Natl. Acad. Sci (USA)* 91:9564–9568 (1994)).

Unfortunately, the VSV-G protein is toxic to cells in which it is expressed. Pseudotyped vector particles have been derived by transient expression of a cassette containing the VSV-G gene after DNA transfection of cells that already express the GAG and POL components of MuLV, yielding vector preparations having titers of $10^5$–$10^6$/ml (Yee, J. K. et al., *Proc. Natl. Acad. Sci (USA)* 91:9564–9568 (1994)). Generation of vector particles by transient expression of the VSV-G gene is cumbersome, labor intensive and unlikely to be amenable to clinical applications that demand reproducible, certified vector preparations. Producer lines are needed in which a silent VSV-G gene is stably integrated in a form that permits reproducible, high level, and inducible expression.

Several inducible promoter systems have been described, including those controlled by heavy metals (Mayo, K. E. et al., Cell 29:99–108 (1982)), RU-486, a progesterone antagonist (Wang, Y. et al., Proc. Natl. Acad. Sci. (USA) 91:8180–8184 (1994)), steroids (Mader & White, Proc. Natl. Acad. Sci. (USA) 90:5603–5607 (1993)) and tetracycline (Gossen & Bujard, Proc. Natl. Acad. Sci. (USA) 89:5547–5551 (1992)). Heavy metals are toxic to cells, eliminating the use of this inducible promoter system. The RU-486 system is interesting, but published reports suggest significant expression of the synthetic promoter in the absence of RU-486 and only a 10–20 fold induction upon addition of this compound (Wang, Y. et al., Proc. Natl. Acad. Sci. (USA) 91:8180–8184 (1994)). Steroids affect the expression of many genes in addition to that of the desired target, but the use of the novel GRE promoter was reported to exhibit 50-fold inducibility. This steroid inducible promoter is based on a glucocorticoid response element (GRE). A synthetic promoter composed of five tandem GRE units, linked to the TATA region of the adenovirus major late promoter, is induced up to 50-fold in the presence of dexamethasone (Mader & White, Proc. Natl. Acad. Sci. (USA) 90:5603–5607 (1993)).

PCT patent publications WO94/29440 and WO92/14829 suggest the production of a stable packaging construct which inducibly expresses the VSV-G protein under the control of the MMTV promoter. This cell line is designed to synthesize glucocorticoid receptor proteins in sufficient amounts to provide for induction of the MMTV promoter in the presence of corticosteroid such as dexamethasone.

The present inventors have found, however, that cell lines transfected with an expression plasmid containing the VSV-G coding sequences under the control of a dexamethasone-inducible promoter, expressed VSV-G proteins only around 30% of the time, and only at relatively low levels. Syncytial formation (a measure of virus production) was rare among the cells of these clones, and the vector titer was estimated at only approximately $10^3$ CFU/ml.

SUMMARY OF THE INVENTION

The invention is based on the inventors' discovery that a tetracycline-responsive promoter is useful, if combined with vesicular stomatitis virus protein G (VSV-G) expression, to derive a retrovirus packaging cell line that inducibly expresses the VSV-G protein at levels sufficient to support high level virus production. It was found that the cell line could produce high titers of retrovirus by avoiding the toxic effects of constitutive expression of VSV-G.

Following the discovery of successful expression with VSV-G, it was also realized that the VSV coding sequences could be replaced with the coding sequences for any viral envelope protein whose expression is toxic in a given cell type, wherein such toxicity limits the production of sufficient amounts of infectious virus in that cell by recombinant genetic expression. Thus, the invention provides packaging cell lines making high amounts of virus with VSV-G or any toxic viral envelope protein.

Further, the invention is more broadly directed to cell lines producing any viral vector requiring a harmful or otherwise undesirable viral protein required for the vector to be produced but detrimentally affecting the cell such that viral production is impaired.

The inducible system generically disclosed herein utilizes components of the tetracycline resistance operon of Tn10 of E. coli. A synthetic promoter composed of at least one copy of the tetracycline operator sequence ($tet^O$), linked to minimal promoter, is controlled by a chimeric transactivator protein ($tet^R$/transactivator) composed of the tetracycline-modulated repressor ($tet^R$) and a transactivator protein. Tetracycline binds to $tet^R$ with high affinity, displacing the chimeric $tet^R$/transactivator from the $tet^O$ sequences, thereby silencing the synthetic promoter.

In a specific disclosed embodiment, the synthetic promoter is composed of seven tandem copies of $tet^O$, the minimal promoter is the cytomegalovirus 1A (CMV 1A) minimal promoter, and the transactivator is the C-terminal activating region of the VP16 protein of the Herpes simplex virus (VP16 transactivator) (Gossen & Bujard, Proc. Natl. Acad. Sci. (USA) 89:5547–5551 (1992)). With this embodiment, removal of tetracycline from the medium results in up to a five log induction of expression of linked genes over 8–12 hours. The level of gene expression can be controlled by varying the concentration of tetracycline in the medium.

The invention is thus directed to retrovirus packaging cell lines containing the following nucleic acid sequences: a nucleic acid sequence coding for a toxic viral envelope protein, the sequence being operably linked to a minimal promoter, which minimal promoter is operably linked to at least one copy of $tet^O$; retrovirus nucleocapsid sequences; chimeric $tet^R$/transactivator coding sequences operably linked to a promoter.

The invention is also directed to producer cell lines. In producer cell lines, the packaging cell further contains a retrovirus-packagable nucleic acid sequence, preferably with one or more heterologous nucleic acid sequences linked thereto. The retrovirus-packagable sequence is introduced into the cell containing the three constructs described immediately above (for packaging cell lines) in order to produce packaged infectious retrovirus.

In such cell lines, retroviral sequences are capable of being packaged with the nucleocapsid proteins. Further, the retroviral sequences that are capable of being packaged may also contain one or more heterologous nucleic acid sequences that are capable of being expressed in a target cell that is infected by the virions produced in the producer cell.

In preferred embodiments, the sequences are one or more of the following: the toxic viral envelope protein is the VSV-G protein, the minimal promoter is the CMV-1A minimal promoter, the transactivator is the C-terminal activating region of the VP16 protein of the Herpes simplex virus. In a highly preferred embodiment, all of these sequences are present.

In the packaging recombinant host cell comprising the VSV-G sequences and the $tet^R$/VP16 transactivator coding sequences, the cell has very low but highly inducible expression of the VSV-G coding sequences, which expression is under control of the $tet^O$/CMV-1A minimal promoter system and can therefore be expressed in a tetracycline dependent manner in the presence of the $tet^R$/VP16 transactivator.

In preferred packaging and producer cells, the toxic envelope protein sequences, nucleocapsid sequences, and $tet^R$/transactivator sequences are all stably integrated in the cell. However, one or more of these sequences could also exist in episomal form and gene expression could occur from the episome.

The invention is also directed to a recombinant nucleic acid sequence comprising a VSV-G coding sequence operably linked to a minimal promoter, which itself is operably linked to at least one copy of tet$^O$.

The invention is also directed to combinations of additional nucleic acid sequences. A preferred combination comprises the toxic viral envelope protein linked to tet$^O$ and the minimal promoter, retrovirus nucleocapsid sequences, and the tet$^R$/transactivator coding sequences operably linked to a promoter. These nucleic acids can be used to construct packaging cell lines. In addition, a retrovirus-packagable nucleic acid sequence may be included. Such a sequence may contain one or more expressible heterologous nucleic acid sequences or cloning sites for such sequences. The addition of such retroviral-packagable sequences allows the construction of producer cells.

In preferred embodiments, the sequences are one or more of the following: the toxic viral envelope protein is the VSV-G protein, the minimal promoter is the CMV-1A minimal promoter, the transactivator is the C-terminal activating region of the VP16 protein of the Herpes simplex virus.

The invention is thus also directed to a combination of nucleic acids comprising a sequence encoding VSV-G, the sequence being operably linked to a minimal promoter, the minimal promoter being operably linked to at least one copy of the tetracycline operator and a sequence encoding a chimeric protein, the protein comprising the tetracycline-modulated repressor and a transactivator protein, wherein the coding sequence is operably linked to a promoter.

The invention is thus directed to methods of making high titer preparations of virions produced in the recombinant producer cells. Viral particles are produced at an infectious titer of $10^6$–$10^7$ CFU/ml and can be concentrated to titers of greater than $10^9$ CFU/ml. The viral envelope protein can be derived from a source different than the source of the packagable retrovirus. When this is the case, the envelope protein may be chosen to have a specific host range different from the host range of the packagable retrovirus. When the envelope contains VSV-G protein, the infectious virions are capable of infecting a broad host range. These infectious units may thus be used to introduce retrovirus or heterologous gene products into a given target cell.

In further preferred embodiments, the $tet^O$ is in seven tandem copies.

In further preferred embodiments, the retrovirus nucleocapsid and nucleic acid sequences capable of being packaged are derived from MoMuLV.

In further preferred embodiments, the host cell is an NIH3T3 cell.

BRIEF DESCRIPTION OF THE FIGURES

FIG. 1. Summary of the plasmids used in the experiments described in the Examples. The construction of the various plasmids is outlined in Materials and Methods in Example I.

FIG. 2(Parts A–D). Morphology and surface immunofluorescence of GP7CN cells transfected 48 hours earlier with pPAM3e (A and B) or pSRα-G (C and D) containing the coding sequences for the MuLV amphotropic or VSV-G envelope proteins, respectively. Cells shown in panels B and D were stained with a monoclonal antibody specific for the VSV-G proteins.

FIG. 3. Strategies used to derive a producer clone inducibly expressing the VSV-G envelope glycoproteins.

FIG. 4(Parts A–B). Expression of VSV-G proteins (panel A) and production of pseudotyped vector particles (panel B) as determined by Western blot analysis of cell lysate or pelleted virus, respectively.

A. Lanes 1–10; lysate from ten clones into which the VSV-G coding sequences had been introduced under the control of a steroid inducible promoter (pGRE5-G). Semi-confluent cells were incubated for 72 hours in 500 nM dexamethasone before preparation of cell lysate. Lane 11: extract from a clone, GP7CN-tTA-G, containing the VSV-G coding sequences under the control of the $tet^R$/VP16 chimeric transactivator. The medium had been changed to remove tetracycline 72 hours before the extract was prepared. Lane (M): extract from cells infected with wild-type VSV.

B. Lanes 1–10: virus particles pelleted from the culture medium of ten clones expressing the VSV-G protein under the control of the $tet^R$/VP16 chimeric transactivator. The cells were grown in semi-confluency and the medium changed to remove tetracycline 72 hours before conditioned medium was harvested for virus preparation. Lane (M): the same extract analyzed in panel A, lane 11, was used as a marker for the migration position of the VSV-G proteins.

FIG. 5. Expression and inducible function of the $tet^R$/VP16 transactivator. A plasmid, pUHD-LacZ, having the β-galactosidase coding sequences under the control of the $tet^O$/CMV-1A minimal promoter was introduced into GP7CN-tTA cells (FIG. 3) by $CaPO_4$ mediated DNA transfection. Extracts were prepared for assay of β-galactosidase after 72 hours of incubation in the presence (+) or absence (–) of 10 μg/ml tetracycline.

FIG. 6. Time course of production of VSV-G pseudotyped vector particles by clone GP7CN-tTA-G4. Cells were grown to semi-confluency in tetracycline (10 μg/ml) and changed into fresh medium lacking tetracycline. Subsequently, the medium was changed at 48 hour intervals and assayed to determine the titer of $neo^R$ particles (CFU/ml). The time intervals shown specify the period following removal of tetracycline, that media was harvested for virus assay. Media harvested at 24, 72, 120 and 168 hours was collected from one set of culture plates and that harvested at 48, 96, 144 and 192 hours from a second set.

FIG. 7(Parts A–B). Morphology of clone GP7CN-tTA-G4 cultured in the presence (A) of tetracycline (10 μg/ml) and 120 hours after replacement with fresh medium lacking tetracycline (B).

DETAILED DESCRIPTION OF THE PREFERRED EMBODIMENTS

Definitions

The term “pseudotype” refers to progeny virions bearing the genome of one virus encapsidated by the envelope protein of another. The assembly of enveloped animal viruses is characterized by selective inclusion of the viral genome and accessory viral proteins into a budding particle.

Several terms herein are used interchangeably. Thus, “virion”, “virus”, “viral particle”, “retroviral particle”, “retrovirus”, and “vector particle” mean virus and virus-like particles that are capable of introducing nucleic acid into a cell through a viral-like entry mechanism. Such vector particles can, under certain circumstances, mediate the transfer of genes into the cells they infect. Such cells are designated herein as “target cells”. When the vector particles are used to transfer genes into cells which they infect, such vector particles are also designated “gene delivery vehicles” or “delivery vehicles”. Retroviral vectors have been used to transfer genes efficiently by exploiting the viral infectious process. Foreign genes cloned into the retroviral genome can be delivered efficiently to cells susceptible to infection by the retrovirus. Through other genetic manipulations, the replicative capacity of the retroviral genome can be destroyed. The vectors introduce new genetic material into a cell but are unable to replicate.

The vector particle includes the following components: the retrovirus nucleic acid, which may contain one or more heterologous genes or other heterologous nucleic acid sequences, a nucleocapsid encapsidating the nucleic acid, the nucleocapsid comprising nucleocapsid protein of a retrovirus, and a membrane surrounding the nucleocapsid. The heterologous nucleic acid sequence may be operably linked to a promoter and encode a protein that is expressible in a target cell.

The term "tetracycline operator" refers to a control element of the tetracycline-resistance operon encoded in Tn10 of *E. coli*. Transcription of genes mediating resistance to tetracycline is negatively regulated by the tetracycline-modulated repressor $tet^R$. In the presence of the antibiotic tetracycline, $tet^R$ does not bind to its operators located within the promoter region of the operon and allows transcription. Tetracycline operator sequences have also been designated $tet^O$. For a further description of the tetracycline operator, please see Hillen, W. et al. in *Protein-Nucleic Acid Interaction, Topics in Molecular and Structural Biology*, Saenger and Hessmann, eds., Macmillan, London (1989), Vol. 10, pages 143–162. The sections describing this operator and its interaction with its repressor are incorporated herein by reference.

The term "tetracycline-modulated repressor" refers to a second control element of the tetracycline-resistance operon encoded in Tn10 of *E. coli*. In the Tn10-specified tetracycline resistance operon of *E. coli*, transcription of resistance mediating genes is negatively mediated by the $tet^R$. The specificity of $tet^R$ for its operator sequence, $tet^O$, as well as the high affinity of tetracycline for $tet^R$ (Takahashi, M. et al., *J. Mol. Biol.* 187:341–345 (1986)) and the well studied chemical and physiological properties of tetracycline, constitutes a basis for the inducible expression system described herein. The $tet^R$ component of the Tn10 specified tetracycline resistance operon is described in detail in Hillen et al., referred to directly above.

The chimeric tetracycline repressor/transactivator (tTA) is composed of a procaryotic tetracycline repressor (first polypeptide) operably linked to a polypeptide which directly or indirectly activates transcription in eucaryotic cells (second polypeptide). Typically, nucleotide sequences encoding the first and second polypeptides are ligated to each other in-frame to create a chimeric gene encoding a fusion protein, although the first and second polypeptides can be operably linked by other means that preserve the function of each polypeptide (e.g., chemically crosslinked). In one embodiment, the second polypeptide is a transcriptional activating protein such as the acidic transactivating domain of virion protein 16 (VP16) of Herpes simplex virus. It should be appreciated that other transactivators, including acidic, proline- or serine/threonine- or glutamine-rich transactivating moieties may be substituted for the VP16 transactivator in the chimeric transactivator. In this embodiment, the second polypeptide of the fusion protein is capable of directly activating transcription.

The term "C-terminal activating region of VP16 (virion protein 16) of Herpes simplex virus" is derived from Labow et al., *Mol. Cell. Biol.* 10(7):3343–3356 (1990) and Baim et al., *Pros. Natl. Acad. Sci. USA* 88:5072–5076 (1991). The relevant portions of these references are incorporated herein by reference. The C-terminal activating region of VP16 of Herpes simplex virus is known to be essential for transcription of the immediate early genes (Triezenberg, J. et al., *Genes Dev.* 2:718–729 (1988).

The term "chimeric protein comprising the tetracycline-modulated repressor and the C-terminal activating region of VP16 of Herpes simplex virus" means a tetracycline-controlled transactivator made by fusing $tet^R$ with the activating domain of VP16 of Herpes simplex virus. This transactivator stimulates transcription from minimal promoter sequence derived from the human cytomegalovirus promoter 1A combined with $tet^O$ sequences. This chimeric protein is described in Gossen, et al. (*Proc. Natl. Acad. Sci. USA* 89:5547–5551 (1992)), which is incorporated herein by reference for this description. The present invention, however, is not limited to the precise chimeric protein described by Gossen et al. but encompasses chimeric transactivators having the essential functions described for the chimeric protein of Gossen et al. Thus, one portion of the chimeric protein functions as a tetracycline-modulated repressor described above and the other portion functions as a transactivator for the CMV minimal promoter. Preferred promoters include, but are not limited to, the SV40 and PGK promoters. In the presence of the antibiotic tetracycline, $tet^R$ does not bind to the operator sequences located within the promoter region of the operon and allows transcription. By combining $tet^R$ with the C-terminal domain of VP16 from HSV, a hybrid or chimeric transactivator is formed which stimulates minimal promoters fused to the $tet^O$ sequences. These promoters are virtually silent in the presence of low concentrations of tetracycline, which prevents the tetracycline-controlled transactivator from binding to $tet^O$ sequences. It is also understood that the transcription of the sequences encoding the chimeric transactivator is not limited to the transcription control sequences constructed by Gossen et al.

The term "minimal promoter" means a partial promoter sequence that defines a transcription start site, but which sequence is incapable of initiating transcription efficiently. The initiation of transcription from such minimal promoters depends upon the binding of a transactivator to a binding site operatively linked to the minimal promoter. For example, as disclosed herein, the minimal promoter of the cytomegalovirus 1A gene is activated by the VP16 transactivator protein. The transactivator protein is joined to the tet repressor. The tet repressor thus binds to the tet operator which is linked to the minimal promoter, allowing activation of transcription from the minimal promoter. The tet repressor is a prokaryotic protein which binds to a tet operator sequence in the absence of tetracycline. This includes repressors of different class types, for example, class A, B, C, D or E tet repressors.

The term "CMV-1A minimal promoter" is described in Gossen et al. cited above. The reference is incorporated herein by reference for its description. The present invention, however, is not limited to the precise minimal promoter described by Gossen et al., but encompasses minimal promoters having the essential function described for the minimal promoter of Gossen et al. A minimal promoter contains a 5' cap site and TATA box which is sufficient to recruit a transcription initiation complex.

The term "heterologous" refers to a nucleic acid sequence or protein sequence linked to a nucleic acid or protein sequence to which it is not naturally linked. A heterologous gene or nucleic acid sequence included in the retroviral genome is thus derived from a source exogenous to the retrovirus. For the purposes of this application, such a heterologous gene or nucleic acid sequence is capable of being expressed from the retrovirus genome either from endogenous retroviral promoters such as a long terminal repeat, or from a heterologous promoter to which the heterologous gene or sequence is operably linked.

The term "toxic" refers to a gene product(s) whose expression detrimentally affects the metabolism of the host cells, thus limiting the quantity of this gene product produced in the host cell. Thus, the term is relevant in the context of using a host cell to produce a gene product. A "host cell" is a cell used specifically to produce the desired toxic gene product.

The term "viral envelope protein" refers to the protein embedded in the membrane which encapsulates the nucleocapsid and which protein is responsible for binding to and entry of the infectious virus into the target cell.

The term "nucleocapsid" refers to at least the group specific antigen (GAG) and the viral polymerase (POL) of a retrovirus genome. These proteins encapsidate the retrovirus-packagable sequences and themselves are further surrounded by a membrane containing an envelope protein.

Recombinant Packaging and Producer Host Cells

The invention is directed to packaging cell lines containing a first nucleic acid sequence, the sequence comprising a nucleic acid sequence encoding a toxic viral envelope protein operatively linked to a minimal promoter, the minimal promoter being operatively linked to at least one copy of $tet^O$, a second nucleic acid sequence encoding a chimeric protein, the chimeric protein comprising $tet^R$ and a transactivator protein, and a third nucleic acid sequence encoding retrovirus nucleocapsid protein, particularly the GAG and POL proteins.

The packaging cell lines are useful for providing the gene products necessary to encapsidate and provide a membrane protein for a retrovirus and retrovirus nucleic gene delivery vehicle. As described below, when retrovirus sequences are introduced into the packaging cell lines, such sequences are encapsidated with the nucleocapsid proteins and these units then bud through the cell membrane to become surrounded in cell membrane and to contain the envelope protein produced in the packaging cell line. These infectious retroviruses are useful as infectious units per se or as gene delivery vehicles.

The invention is thus directed to a cell containing a fourth nucleic acid sequence comprising retroviral sequences capable of being packaged in the nucleocapsid protein. Such cells are useful for producing infectious retrovirus. Further, the retroviral sequence can contain at least one heterologous nucleic acid sequence linked to the retroviral sequences, and which heterologous nucleic acid sequence is capable of being expressed in a target cell. Thus, the cells are useful to produce infectious retrovirus and retroviral gene delivery vehicles. Such cells are also designated "producer" cells.

In preferred embodiments, the minimal promoter is the CMV-1A promoter. In further preferred embodiments, the toxic envelope protein is the VSV-G protein. In further preferred embodiments, the transactivator protein is the C-terminal activating region of the VP16 protein of Herpes simplex virus. In a most preferred embodiment, the minimal promoter is the CMV-1A promoter, the toxic envelope protein is the VSV-G protein, and the transactivator is the C-terminal activating region of the VP16 protein of Herpes simplex virus. In a specific disclosed embodiment, a packaging cell line is provided, said cell line having an ATCC accession number of ATCC CRL-11874, deposited Apr. 13, 1995 under the terms of the Budapest Treaty with the international Depository Authority American Type Culture Collection at the address of 12301 Parklawn Drive, Rockville, Md. 20852, U.S.A.

Retrovirus vectors thus produced in the cells of the invention are important tools for stable gene transfer into cells, and particularly, into mammalian cells. They facilitate gene transfer for use in gene therapy. These vectors are useful for transferring genes efficiently by exploiting the viral infectious process. Foreign genes cloned into the retroviral genome can be delivered efficiently to cells susceptible to infection by the retrovirus. Through genetic manipulations, the replicative capacity of the retroviral genome is destroyed so that the vectors introduce new genetic material to a cell but are unable to replicate. Furthermore, by the choice of the viral envelope protein, the range of cells that can be infected by these viruses can be controlled. Accordingly, such infectious retrovirus can be used to infect mammalian and non-mammalian species depending upon the choice of envelope protein. Further, when the retrovirus genome contains an expressible heterologous gene, expression in a target cell can be controlled by a tissue-specific promoter.

The use of retroviral vectors for gene therapy has been extensively reviewed. For example, see, Miller, A. D. et al., *Biotechniques* 7:980–987 (1989), Miller, A. D., *Human Gene Therapy* 1:5–14 (1990), Cornetta, K. et al., *Human Gene Therapy* 2:5–14 (1991), Plautz, G. et al., *The New Biologist* 5:709–715 (1991) and Gruber, H. et al., WO91/02805.

Although the experimental work disclosed herein is directed to cell lines for producing infectious, recombinant retroviral vectors, the concepts and design are broadly applicable to cell lines for the production of any viral vector where harmful or otherwise undesirable viral proteins must be produced by the cell in order for the viral vector to be produced. The constructs and methods of invention are used to prevent or minimize the production of these proteins until they are needed. At that time, expression is induced for a period of time necessary for the production of the proteins and the assembly of the viral vectors. Examples of such viral vectors include other RNA viral vectors besides retroviral vectors, and DNA viral vectors, such as adenoviral vectors, adeno-associated viral vectors, Herpesvirus vectors (preferably Herpes simplex I virus vectors), and vaccinia virus vectors. Examples of harmful or undesirable proteins include, for adenoviral vectors, products of the E1, E2, E4, and major late genes; for adeno-associated viruses, the rep protein; and for Herpesvirus, the capsid protein. Methods for the construction of such cell lines will be readily apparent to those skilled in the art, given the teachings contained herein. A preferred application of this approach would be the induction of the E2 and E4 adenoviral proteins in the cell lines disclosed in U.S. patent application Ser. No. 08/355,087, "Improved Adenoviral Vectors and Producer Cells," incorporated herein by reference.

Nucleic Acid Sequences

The invention is directed to a nucleic acid sequence that expresses the VSV-G coding sequence operably linked to a minimal promoter, the minimal promoter being operably linked to at least one copy of $tet^O$. In a preferred embodiment, the minimal promoter is derived from CMV-1A promoter.

In a preferred embodiment of the invention, the VSV-G expression cassette is in the plasmid known as pUHD10-G, described herein.

The invention also encompasses a combination of nucleic acids, for example, provided in kit form.

The combination encompasses nucleic acids comprising a sequence encoding a toxic viral envelope protein, the sequence operably linked to a minimal promoter, the minimal promoter being operably linked to at least one copy of the tetracycline operator, a sequence encoding a chimeric protein, the chimeric protein comprising a tetracycline-modulated repressor and a transactivator protein, the coding sequence being operably linked to a promoter, and a nucleic acid sequence encoding retrovirus nucleocapsid proteins.

In preferred embodiments, one or more of the following is present: the minimal promoter is the CMV-1A minimal promoter, the transactivating protein is the C-terminal activating region of the VP16 protein of Herpes simplex virus, and the toxic envelope protein is VSV-G.

The combination can also include retroviral sequences capable of being encapsidated in the retrovirus nucleocapsid proteins. These retroviral sequences could further contain one or more heterologous nucleic acid sequences or cloning sites wherein one or more heterologous sequences can be inserted.

The invention also comprises a combination of nucleic acids comprising a sequence encoding VSV-G, the sequence being operably linked to a minimal promoter, the minimal promoter being operably linked to at least one copy of the tetracycline operator and a sequence encoding a chimeric protein, the protein comprising the tetracycline-modulated repressor and a transactivator protein, wherein the coding sequence is operably linked to a promoter.

The nucleic acid sequences of the invention may be in the form of double- or single-stranded DNA, including genomic DNA and cDNA. Alternatively, the nucleic acid sequence may be in the form of RNA.

The nucleic acid sequences can occur in isolated form or linked to recombinant propagation or delivery vehicles, such as RNA and DNA phages, RNA and DNA viruses, plasmids and other episomal elements.

The invention is also directed to a procaryotic or eucaryotic cell containing a nucleic acid sequence comprising a nucleic acid sequence encoding a toxic viral envelope protein, and particularly, the VSV-G protein, operably linked to a minimal promoter, said minimal promoter being operably linked to at least one copy of $tet^O$. Such cells are useful for propagating the nucleic acid sequence.

Methods of Making Recombinant Host Cells

The invention is also directed to methods of making recombinant host cells by introducing one or more of the nucleic acids described above into a desired cell. The desired nucleic acids may be introduced into the host cell by means well-known in the art.

Methods for introducing the above-described nucleic acid sequences into host cells to form recombinant packaging or producer cells are known in the art. For example, see, U.S. Pat. Nos. 4,405,712; 4,650,764; 4,861,719; and 5,124,263, all herein incorporated by reference as describing such means of introducing the nucleic acid sequences into a host cell.

Methods of Using the Recombinant Host Cells

The invention also provides methods for producing infectious retrovirus particles containing a toxic envelope protein, and especially the VSV-G protein, as the envelope protein. Accordingly, cells containing the desired expression cassette, $tet^R$/transactivator, retrovirus nucleocapsid proteins, and packagable retrovirus sequences, are incubated in cell culture medium lacking tetracycline.

The cells are useful for producing infectious pseudotyped retrovirus, and especially high titer virions which may also contain one or more heterologous nucleic acid sequences capable of being expressed in a target cell or tissue. The cells are thus useful for packaging a retrovirus genome which may also contain a heterologous nucleic acid sequence capable of being expressed in a target cell or tissue.

When the expression cassette is to be induced, tetracycline is removed from the cell culture medium so that the quantity of tetracycline is insufficient to prevent transcription from the $tet^O$/minimal promoter. Preferably, all detectable tetracycline is removed. However, it is to be understood that transcription from the minimal promoter can be controlled by varying the levels of tetracycline in the cell culture medium.

When the viral particles are enveloped in the VSV-G protein, the retrovirus produced by the cells of the invention is useful for infecting a broad host range of cells. Thus, the invention provides a virion capable of infecting a broad variety of cell types and, if desired, of delivering specific nucleic acid sequences and gene products to such cell types. It is also to be understood that alteration of the host range can be affected by toxic envelope proteins, which alterations include not only broadening but changing a narrow host specificity to a different but equally narrow host specificity.

Further Embodiments for Cells and Methods of Using the Cells

One or more of the nucleic acid sequences described above are stably integrated in the cell. However, embodiments are possible in which transient expression may be desired for one or more of these sequences. In highly preferred embodiments, the toxic envelope protein expression cassette, and particularly the VSV-G expression cassette, is stably integrated in the cell. In a specific disclosed embodiment, all of the nucleic acid constructs are integrated. This includes the VSV-G expression cassette, $tet^R$/VP16, nucleocapsid, and retroviral genome. If one or more of the constructs is in episomal form, the vector could include Epstein Barr Virus or papilloma virus. Further, the system can be used to achieve modulatable expression of a particular gene even when the DNA is introduced in the context of a transient expression system.

In preferred embodiments, the minimal promoter is operably linked to more than one tandem copy of $tet^O$ and preferably to seven tandem copies of $tet^O$. However, greater than seven copies are also included.

In preferred embodiments of the invention, the nucleocapsid proteins are derived from Moloney murine leukemia virus. However, the invention also encompasses, but is not limited to, Harvey murine sarcoma virus.

In preferred embodiments of the invention, the host cell type is the cell line known as "NIH3T3" (ATCC Accession No. CRL-1658). In a more preferred embodiment, the NIH3T3 cell is TK⁻. Methods for making NIH3T3 TK⁻ cells are well known in the art. However, potentially, any cell type capable of expressing the relevant gene products is included in the invention. Such cell types include, but are not limited to, 293, HeLa, COS, human fibroblasts, and human leukemia cells. The latter include, for example, CCRF-CEM (ATCC CCL 119), IM-9 (ATCC CCL 159) and K-562 (ATCC CCL 243).

As described herein, the promoter for the $tet^R$/VP16 chimeric transactivator protein is derived from the CMV-1A gene. However, potentially, any promoter could be used. Examples of such promoters include, but are not limited to, SV40, β-globin, RSV LTR, mammalian PGK, β-actin, and MoMuLV LTR.

Although the cells described herein produce retrovirus solutions of titers in the range $10^5$–$10^7$ CFU/ml in the culture medium, such particles can be concentrated further by standard concentration techniques to achieve titers in the range of $10^8$–$10^9$ CFU/ml.

In preferred embodiments, the concentrating step is ultracentrifugation, filtration, or chromatography. The pellet may also be resuspended in a liquid and subjected to a second cycle of ultracentrifugation. The vector particles disclosed herein can be concentrated to a titer of at least $10^8$–$10^9$ CFU/ml.

Potentially, any heterologous nucleic acid sequence could be included in the recombinant retroviral particle. Preferred genes or classes of genes include those that provide immunologically detectable cell surface markers, drug resistance genes (e.g., DHFR), human enzymes (e.g., glucocerebrosidase), and human globin. It is also understood that the heterologous nucleic acid sequence could express not only functional protein but also RNA, such as anti-sense RNA.

In preferred embodiments of the invention, the retrovirus sequences that are capable of being encapsidated in the cells of the invention are derived from Moloney murine leukemia virus. However, potentially any retrovirus sequence could be used. Such retroviruses include, but are not limited to, the MSV family, other members of the MLV family, and lentivirus, such as HIV and ALV. Further, the retrovirus sequences that are encapsidated may be derived from a retrovirus different from the retrovirus from which the nucleocapsid sequences are derived.

Although the invention is based upon results obtained with VSV-G, it is to be understood that the invention also encompasses the use of tet$^O$/minimal promoter system to inducibly express other genes than VSV-G. Thus, the use of this inducible system to produce large quantities of otherwise toxic proteins can be accomplished by substituting a desired coding or non-coding sequence for the VSV-G coding sequence. Such a sequence could be used to express other envelope proteins which may be useful for producing pseudotyped virions but which may be toxic to the cell when expressed constitutively. Examples of such envelope proteins include, but are not limited to, HIV-1, HTLV-1, and influenza virus envelope proteins.

In specifically disclosed embodiments of the invention, the plasmid pUHD10-G provides the VSV-G expression cassette.

In specifically disclosed embodiments of the invention, the recombinant host cell providing infectious pseudotyped virions containing the VSV-G envelope protein is designated GP-7C-tetVP16-G, deposited as ATCC CRL-11874.

Having now generally described the invention, the following examples illustrate the compositions and methods of the present invention.

EXAMPLE 1

Materials and Methods

Plasmids and Cell Lines

The functionally relevant segments of various plasmids used in these experiments are shown diagrammatically in FIG. 1 and their construction is described below.

G1Na contains the Neo$^R$ coding sequences under the control of the Moloney MuLV promoter in a vector backbone engineered for clinical safety (McLachlin, J. R. et al., Virol. 195: 1–5 (1993)).

pPAM3e was derived from the plasmid, pPAM3 (Miller & Buttimore, Mol. Cell. Biol. 6:2895–2902 (1986)) by digestion with BglII and religation to delete the GAG and POL encoding sequences leaving the ENV sequences under the control of the Moloney MuLV promoter. See also U.S. Pat. No. 4,861,719, incorporated herein by reference.

pSVGL1 contains an expression cassette for VSV-G under the control of the SV40 early promoter (Rose & Bergmann, Cell 30:753–762 (1982)).

pSRα-G was constructed by inserting a 1664 bp Xho1 fragment containing the VSV-G coding sequences (Rose & Gallione, J. Virol. 39:519–528 (1981)) into an expression plasmid having a hybrid promoter containing segments of the SV40 early promoter and the HTLV LTR (Takebe, Y. et al., Mol. Cell. Biol. 8:466–472 (1988)).

pUHD15-1 contains the chimeric tet$^R$/VP16 transactivator coding sequences under the control of the CMV1A promoter (Gossen & Bujard, Proc. Natl. Acad. Sci. (USA) 89:5547–5551 (1992)).

ptet$^O$-LacZ was constructed by inserting the 439 bp Xho1-SacII fragment from pUHD10-3, which contains the heptameric tet$^O$ sequences and the CMV 1A promoter (Gossen & Bujard, Proc. Natl. Acad. Sci. (USA) 89:5547–5551 (1992)), upstream of the LacZ gene in p610ZA (Kothary, R. K. et al., "Transgenes as molecular probes of mammalian developmental genetics," in Oxford Surveys on Eukaryotic Genes, Vol. 6, N. Maclean, ed., Oxford Press (1989), pp. 145–178).

The construction of pUHD-puro2 required multiple steps. The 630 bp ClaI-HindIII from pJ6Ωpuro (Morgenstern and Land, Nuc. Acids Res. 18:3587–3596 1990)), containing the puro$^R$ gene (Vara et al., Nucleic Acids Res. 14:4617–4624 (1986)), was inserted into pIC20R (Marsh, J. L. et al., Gene 32:481–485 (1984)), thereby flanking the puro$^R$ gene with EcoRI sites. The EcoRI fragment containing the puro$^R$ was then ligated into pUHD10S (Fornerod, M. et al., Oncogene (in press) (1995) to give pUHD-puro1. pUHD-puro1 contains a SphI site which includes the ATG trinucleotide as part of its recognition sequence, immediately 5' to the puro$^R$ gene. The SphI was removed by partial digestion with SalI followed by complete digestion with HindIII, blunting of the sites and relegation.

pUHD10-G was constructed by inserting a 1665 bp EcoRI fragment containing the VSV-G coding sequences into pUHD-10S (Fornerod, M. et al., Oncogene (in press) (1995)).

pTK5-109 was constructed by inserting the coding sequences for thymidine kinase (McKnight, S. L., Nucleic Acids Res. 8:5949–5964 (1980)) into a plasmid containing the Herpes simplex promoter for this gene.

pGRE5-G was constructed by inserting a 1665 bp EcoRI containing the VSV-G coding sequences (Rose & Gallione, J. Virol. 39:519–528 (1981)) into pGRE5-1 (Mader & White, Proc. Natl. Acad. Sci. (USA) 90:5603–5607 (1993)).

pM2-puro was made by ligating a SnaBI-NheI fragment isolated from pBabe-puro (Morgenstern & Land, Nuc. Acids Res. 18:3587–3596 (1990)), which contains the SV40 promoter and puro$^R$ gene (approximately 1,000 bp), into the SnaBI and NheI sites of pMET2-PA (M. A. Eglitis and J. A. Thompson, personal communication).

GP7C (obtained from Genetic Therapy, Inc., Gaithersburg, Md.), a cell line that constitutively expresses the GAG- and POL-encoded components of the Moloney MuLV under the control of the SV40 early promoter was derived by introducing the plasmid, pM2-SVGP, into thymidine kinase deficient (TK⁻) 3T3 cells by co-transfection with pHR5, a plasmid containing a transcription cassette that confers resistance to hygromycin (Rhee, S. S. et al., *J. Virol.* 64:3844–3852 (1990)). The construction of pM2-SVGP required multiple steps. Initially, a 5131 bp PstI-ScaI fragment from pMLV-K (Miller & Verma, *J. Virol.* 49:214–222 (1984)), containing the entire POL gene and the majority of the GAG gene, was inserted into pUC18 to give pUC-ΔGP. pUC-GP, which also contains the 5' end of the GAG gene, together with a consensus Kozak sequence (Kozak, M., *J. Mol. Biol.* 196:947–950 (1987)) was constructed by inserting a 141 bp sequence (using 4 overlapping oligos) into the PstI site of pUC-ΔGP. The entire GAG/POL coding region from pUC-GP was then inserted into the SnaBI site of pMET2-PA (obtained from Genetic Therapy, Inc.) as a blunted EcoRI fragment and the SV40 promoter from LNSX (Miller & Rosman, *BioTechniques* 7:980–990 (1989)), as a blunted BamHI-HindIII fragment, was then cloned into the NotI (blunted) site to give pM2-SVGP.

An amphotropic clone (G1Na.40) producing the vector, G1Na, that contains the neo$^R$ gene (Jimenez & Davies, *Nature* 287:869–871 (1980)), was obtained from Genetic Therapy, Inc. All cell lines and their derivatives were maintained in high-glucose Dulbecco's modified essential medium (DMEM) supplemented with 10% fetal calf serum, 2 mM L-glutamine, penicillin (100 units/ml) and streptomycin (100 µg/ml) and maintained at 37° C. in 5% $CO_2$.

DNA Transfection and Selection of Clones

Plasmid DNA was prepared by standard techniques including two bandings in a $CsCl_2$ gradient (Sambrook, J. et al., *Molecular Cloning: A Laboratory Manual*, Cold Spring Harbor Laboratory, Cold Spring Harbor, N.Y. (1990)). It was introduced into cells by calcium phosphate ($CaPO_4$) mediated DNA transfection using conventional techniques (Wigler, M. et al., *Cell* 14:725–731 (1978)). Semi-confluent cells were exposed to $CaPO_4$ precipitated DNA for twelve hours. The cells were then washed with phosphate buffered saline (PBS) and maintained in fresh culture medium. After 48 hours, when the cells had become confluent, they were split from 1:5 to 1:500 to allow selection of individual colonies by limiting dilution. Selection was imposed by adding G418 (500 µg/ml, active), puromycin (5 µg/ml) or hypoxanthine, aminopterin-thymidine (1×HAT) medium (GIBCO, Gaithersburg, Md.) as appropriate. Tetracycline was added at a concentration of 10 µg/ml when needed to repress activity of the tet$^R$/VP16 transactivator. After 14–21 days, individual colonies were recovered by trypsinization and expanded to obtain clonal cell lines.

Protein Expression. Surface expression of VSV-G glycoprotein was evaluated by immunofluorescence analysis using a specific monoclonal antibody. Cells were grown to subconfluent density on glass coverslips in 35 mm tissue culture dishes. Forty-eight hours after $CaPO_4$ mediated DNA transfer of an expression plasmid, the medium was removed, the cells washed twice with PBS and fixed by adding paraformaldehyde solution (3% paraformaldehyde/ 2.5 mM NaOH in PBS, pH 7.4) and incubated for 20 minutes at room temperature. The coverslips were inverted over 75 µl of a 1:200 dilution of the anti-VSV-G monoclonal antibody 11 (Jackson ImmunoResearch, Westgrove, Pa.) in PBS containing 10 mM glycine. After 10 minutes at room temperature, the slides were washed and exposed to Rhodamine-conjugated goat anti-mouse antibody (Jackson ImmunoResearch, Westgrove, Pa.) (1:50 dilution in PBS-glycine) for 10 minutes. The coverslips were washed with PBS, dried and mounted on microscope slides for viewing.

Western blot analysis to detect and quantitate VSV-G protein expression in cell lysate or culture medium was performed using conventional techniques (Sambrook, J. et al., *Molecular Cloning: A Laboratory Manual*, Cold Spring Harbor Laboratory, Cold Spring Harbor, N.Y. (1990)). Cell lysates were prepared from $1 \times 10^6$ pelleted cells by addition of 100 µl of lysis buffer (10 mM Tris, pH 7.4, 66 mM EDTA, pH 7.4, 1% Triton X-100, 0.4% Na-deoxycholate, 0.02% $NaN_3$). After 2 min at room temperature, cell lysates were transferred to microcentrifuge tubes and centrifuged for 1 min at 14,000 rpm. Thirty microliters of cleared supernatant were prepared for the electrophoresis by adding 9 µl of buffer (22 mM Tris-HCl, pH 6.8, 5.3% glycerol, 11% SDS, 0.11% Bromphenol blue, 20% 2-ME). Vector particles were collected from 1 ml of culture medium from cells grown to confluency in 60-mm plates. The media was filtered through 0.45 µm filters and centrifuged in a Sorvall F-28/micro rotor at 20,000 rpm at 4° C. for sixty minutes. The pellet was resuspended in 20 µl of buffer (125 mM Tris-HCl, pH 7.5, 4% SDS, 10% glycerol, 0.02% bromphenol blue). Electrophoresis was performed on 10% SDS polyacrylamide gels after which proteins were electroblotted onto nitrocellulose membranes. Each membrane was probed with a 1:1000 dilution of the specific rabbit anti-VSV sera (Lee Biomolecular Research, Inc. San Diego, Calif.) in serum incubation buffer (150 mM NaCl, 50 mM Tris, pH 7.4, 1 mM EDTA, pH 7.4, 0.05% Tween-20, 0.1% BSA). After 1.5 hours at room temperature, the membranes were washed three times in washing buffer (150 mM NaCl, 50 mM Tris, pH 7.4, 1 mM EDTA, 0.05% Tween-20) and exposed to a 1:600 of the HRP-conjugated donkey anti-rabbit antibody (Jackson ImmunoResearch, Westgrove, Pa.) in washing buffer. After one hour at room temperature, the membranes were washed for three times in washing buffer, then transferred into detection solution (50 mM Tris/0.2M NaCl, pH 7.4, 0.5mg/ml 4-chloro-1-naphthol, 0.001% $H_2O_2$)and incubated for 5–20 min at room temperature until color formation occurred.

β-galactosidase activity was detected in cells transfected with the ptet$^O$-LacZ plasmid (FIG. 1). Forty-eight hours after $CaPO_4$ mediated DNA transfer, cells were harvested and an extract prepared from $1 \times 10^7$ pelleted cells in the lysis buffer (Stratagene, La Jolla, Calif.). An assay for β-galactosidase activity was performed according to the instructions provided with the assay kit (Stratagene, La Jolla, Calif.).

Virus Production, Concentration and Titering. Culture media was removed from semi-confluent producer cells at various times following removal of tetracycline to allow induction of the VSV-G protein expression, and filtered through a 0.45 µm filter before further processing. For concentration, this medium was subjected to ultracentrifugation in a SW41 or SW28 rotor at 50,000×g (90 min, 4° C.). The pelleted virus was resuspended in an amount of 50 mM Tris-HCl, pH 7.8, 130 mM NaCl, 1 mM EDTA buffer by incubation at 4° C. for 14–20 hours to potentially achieve a 200-fold or greater concentration of vector particles.

A rough estimate of vector titer in culture medium was obtained by RNA slot blot analysis. The viral particles in 1 ml of culture medium was precipitated by adding 0.5 ml of PEG solution (30% PEG 8000, 1.5M NaCl). After 30 min on ice, the samples were centrifuged for 5 min at 4° C. The pellets were resuspended in 0.2 ml VTR buffer (10 mM Tris-HCl, pH 8.0, 1 mM EDTA, pH 8.0, 20 mM Vanadyl Ribonucleoside Complex [VRC], 100 µg/ml yeast tRNA), and then lysed by adding 0.2 ml of 2×lysis buffer (1% SDS, 0.6M NaCl, 20 mM EDTA, 20 mM Tris, pH 7.4). The viral RNA was extracted once with phenol and chloroform and precipitated with ethanol. The RNA pellets were dissolved in 0.25 ml of 15% formaldehyde solution after which 0.25 ml of 20×SSC was added. The RNA samples were then loaded onto a membrane using a slot blot apparatus (Schleicher & Schuell, Keene, N. H.) with slight vacuum. After loading, the membrane was removed, rinsed in 10×SSC, air dried, baked at 80° C. for 2 hours under vacuum and prehybridized in the hybridization solution (10% dextran sulfate, 1% SDS, 1M NaCl) at 60° C. for 2 hours. Hybridization was performed by probing the membrane with a nick translated, [$^{32}$P] labelled restriction fragment derived from the neo$^R$ gene at 60° C. for 12–16 hours. After washing at 60° C. in 2×SSC for 30 min and in 0.5×SSC for a further 30 min, the membrane was dried and imaged by autoradiography.

Functional assays of viral titer were obtained by estimating the concentration of neo$^R$ colony forming units (CFU/ml). 3T3 cells were seeded at 5×10$^5$ cell into 10-cm tissue culture plates and incubated for 24 hours. Culture medium or concentrated virus was diluted in 10-fold decrements in culture medium containing 6 µg/ml polybrene (Sigma, St. Louis, Mo.) and added to culture plates after which the incubation was continued for another 24 hours. Then the culture medium was removed and replaced with medium containing G418 (500 µg/ml, active). After 14 days, the plates were stained with crystal violet and the individual colonies enumerated to provide an estimate of viral vector titer (neo$^R$ CFU/ml). Neutralization assays were performed by incubating culture medium containing vector particles with various dilutions of rabbit anti-VSV serum (Lee, Biomolecular Research Laboratory, Inc., San Diego, Calif.) at 37° C. for 30 minutes prior to titering.

Results

Production of Pseudotyped Vector Particles During Transient Expression of VSV-G Proteins in GP7C Cells A retroviral vector genome containing the neo$^R$ gene (G1Na) was introduced into GP7C cells by exposure of cells to culture medium from a producer clone generating amphotropic vector particles (G1Na.40, Genetic Therapy Inc.). Individual clones were isolated by G418 selection and culture media from each was assayed for content of vector RNA by RNA slot blot analysis. A clone designated GP7CN, which gave the highest signal, was selected for subsequent experiments.

Figure 2A:
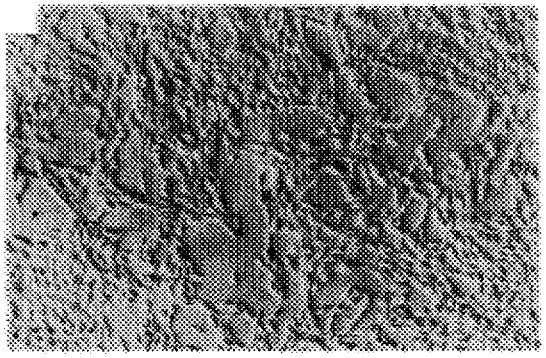
Figure 2C:
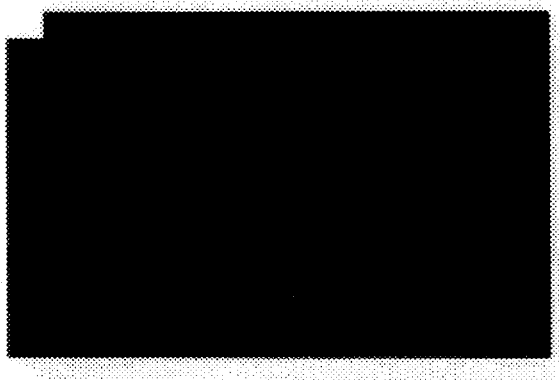
Figure 2B:
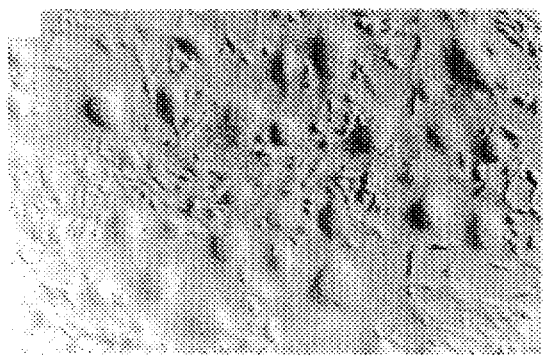
Figure 2D:

Semi-confluent GP7CN cells were transfected with an expression plasmid encoding the amphotropic envelope protein (pPAM3e) or the VSV-G protein (pSVGL1 or pSRα-G) (FIG. 1). Within 48–72 hours, extensive syncytial formation was detected among cells transfected with pSRα-G (FIG. 2B) whereas fewer syncytia were seen by cells transfected with pSVGL1 and none by cells transfected with pPAM3e (FIG. 2A) or a control plasmid (pUC19). Approximately 30–50 percent of cells transfected with pSRα-G exhibited membrane VSV-G expression as determined by immunofluorescence (FIG. 2D); multinucleated syncytia were all brightly fluorescent. Fewer cells transfected with pSVGL1 were positive by immunofluorescence for VSV-G protein whereas control cells transfected with pPAM3e (FIG. 2C) or an irrelevant plasmid (PUC19) were negative in the immunofluorescence assay. Culture media harvested 72–96 hours following transfection of GP7CN cells with pSRα-G contained 10$^4$–10$^5$ neo$^R$ CFU/ml. The vector particles could be concentrated up to 200-fold by ultracentrifugation with nearly 100 percent recovery (data not shown). Infection of 3T3 cells by VSV-G pseudotyped vector particles was completely blocked by pre-incubation in anti-VSV serum (Table I).

Figure 3:
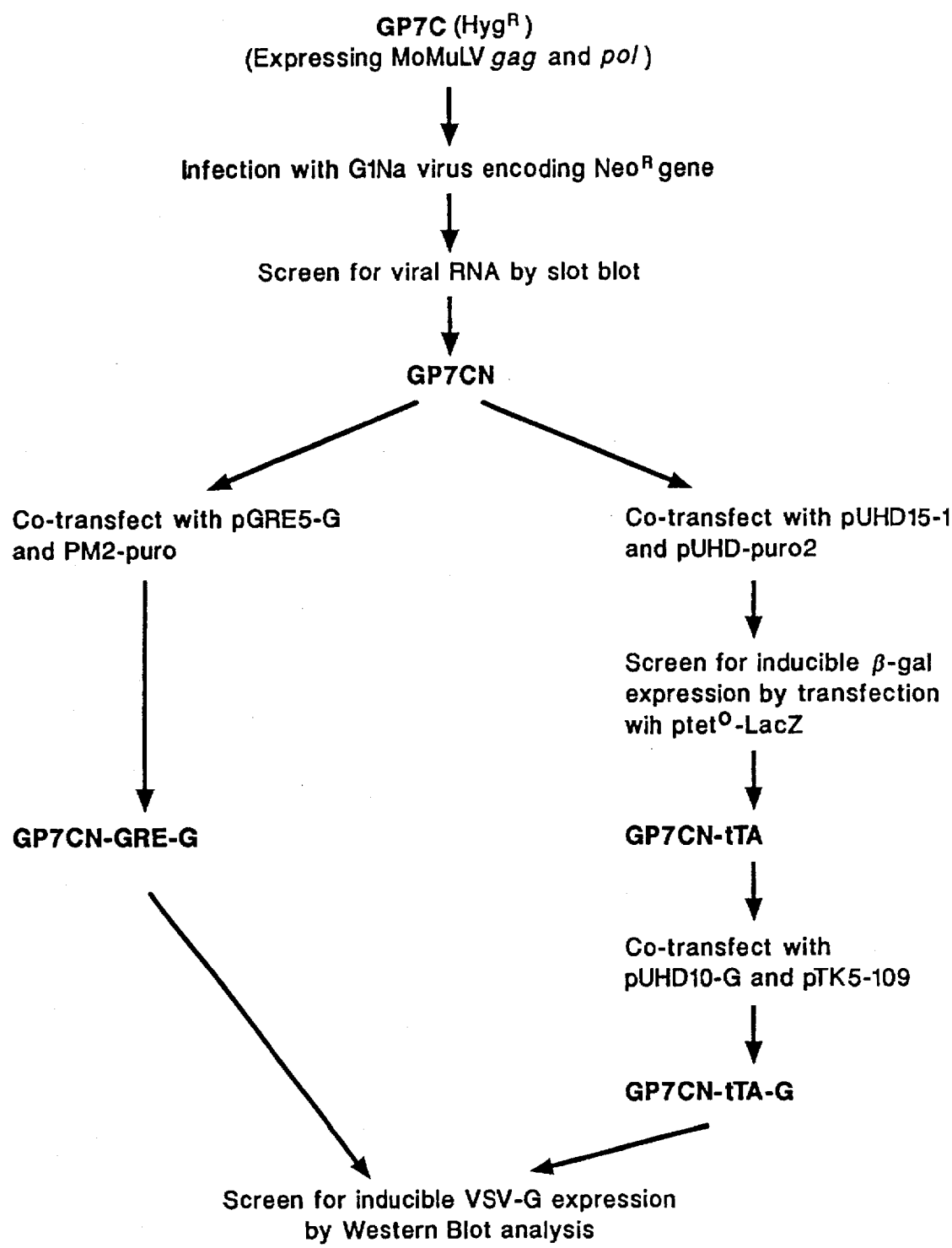
Figure 4A:
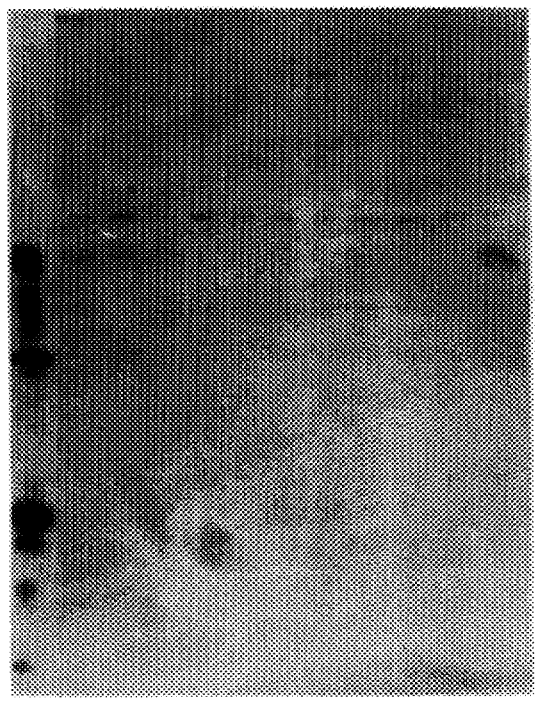

Derivation of Retroviral Vector Producer Clones Inducibly Expressing VSV-G Proteins FIG. 3 diagrams strategies to achieve high level, inducible VSV-G protein expression in vector and producer cells. The plasmids used in these experiments are outlined in FIG. 1. The primary screen of candidate clones was by Western blot analyses of cell lysate (FIG. 4A).

Among the 34 clones transfected with pGRE5-G (containing the VSV-G coding sequences under the control of a dexamethasone inducible promoter (FIG. 1)), only ten expressed the VSV-G proteins and then only at relatively low levels. Syncytial formation was rare among the cells of these clones and the vector titer was estimated at only approximately 10$^3$ neo$^R$ CFU/ml.

Figure 5:
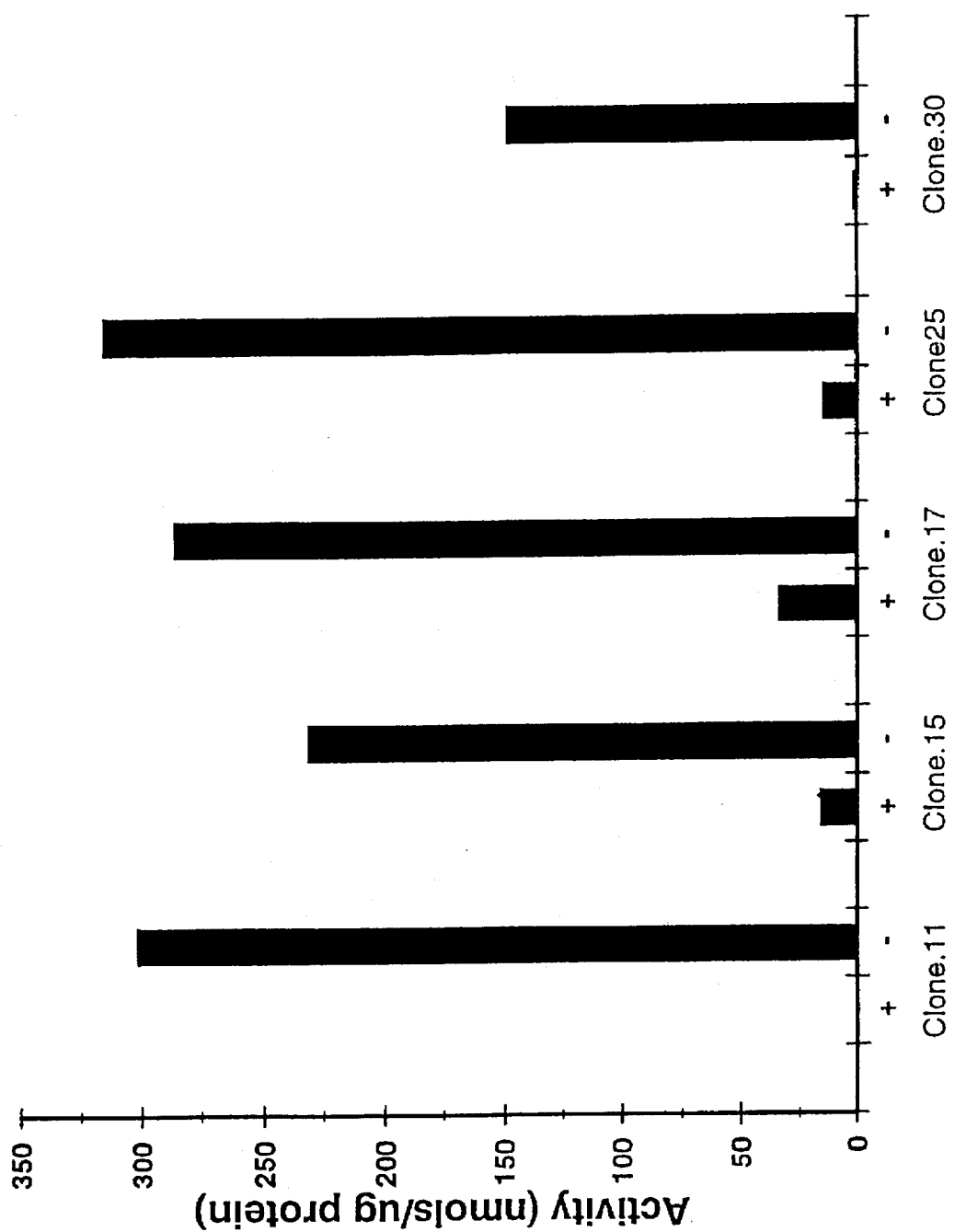

Positive results were obtained, however, using components of the tetracycline resistance operon. The first step in deriving cells inducibly expressing VSV-G, using components of the tetracycline resistance operon, was the introduction of a plasmid (pUHD15-1) expressing the chimeric tet$^R$/VP16 transactivator (tTA) into GP7CN cells (FIGS. 1 and 3). To ensure that all clones expressed the chimeric transactivator, we used a "puromycin trap" strategy in which the puro$^R$ coding sequences were under control of the tet$^O$ minimal promoter (pUHD-puro2). Several clones were isolated and further screened for inducible function of the tet$^R$/VP16 in a transient assay following transfection with a plasmid containing the α-galactosidase coding sequences under the control of the tet$^O$ minimal promoter (ptet$^O$-LacZ). A clone designated GP7CN-tTA that exhibited low α-galactosidase activity on assay of lysate from cells incubated with tetracycline and high levels in lysate of cells incubated without tetracycline (FIG. 5, clone 11) was selected for further use.

Figure 4B:
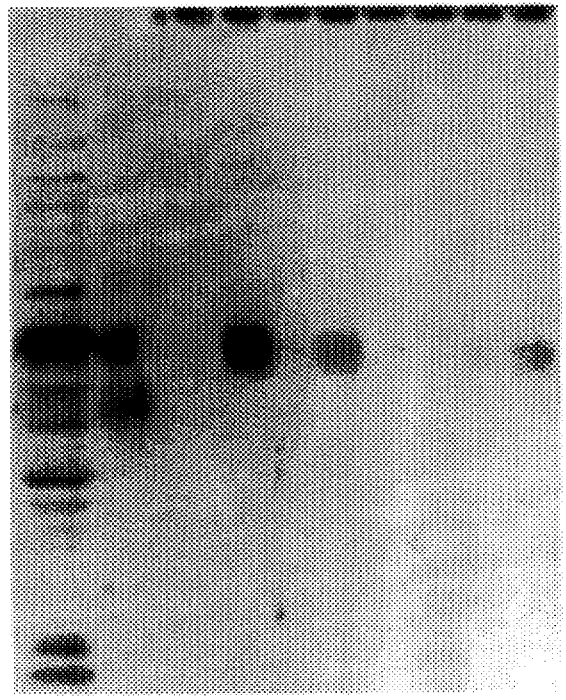

The VSV-G coding sequences under the control of the tet$^O$/CMV-1 minimal promoter were introduced into GP7CN-tTA cells using the thymidine kinase marker for selection (FIG. 3). Forty individual clones were isolated in medium containing tetracycline (10 µg/ml). Seventy-two hours after removal of tetracycline, cell lysates were prepared from each clone and assayed for VSV-G expression by Western blot analysis (FIG. 4A). Noteworthy, is that several of the cell clones exhibited prominent syncytial formation when cultured in the absence of tetracycline. VSV-G protein was detected in cell lysates of these clones at variable levels; one clone designated GP7CN-tTA-G4, exhibited particularly high expression. Vector particles present in media conditioned by each of the clones was concentrated by ultracentrifugation and assayed by Western blot analysis. Again, clone GP7CN-tTA-G4 exhibited the highest amount of particle associated VSV-G protein (FIG. 4B, Lane 4). In the presence of tetracycline, clone GP7CN-tTA-G4 grew with a doubling time of 18–24 hours.

Pseudotyped Vector Production Following Induced VSV-G Protein Expression

Figure 6:
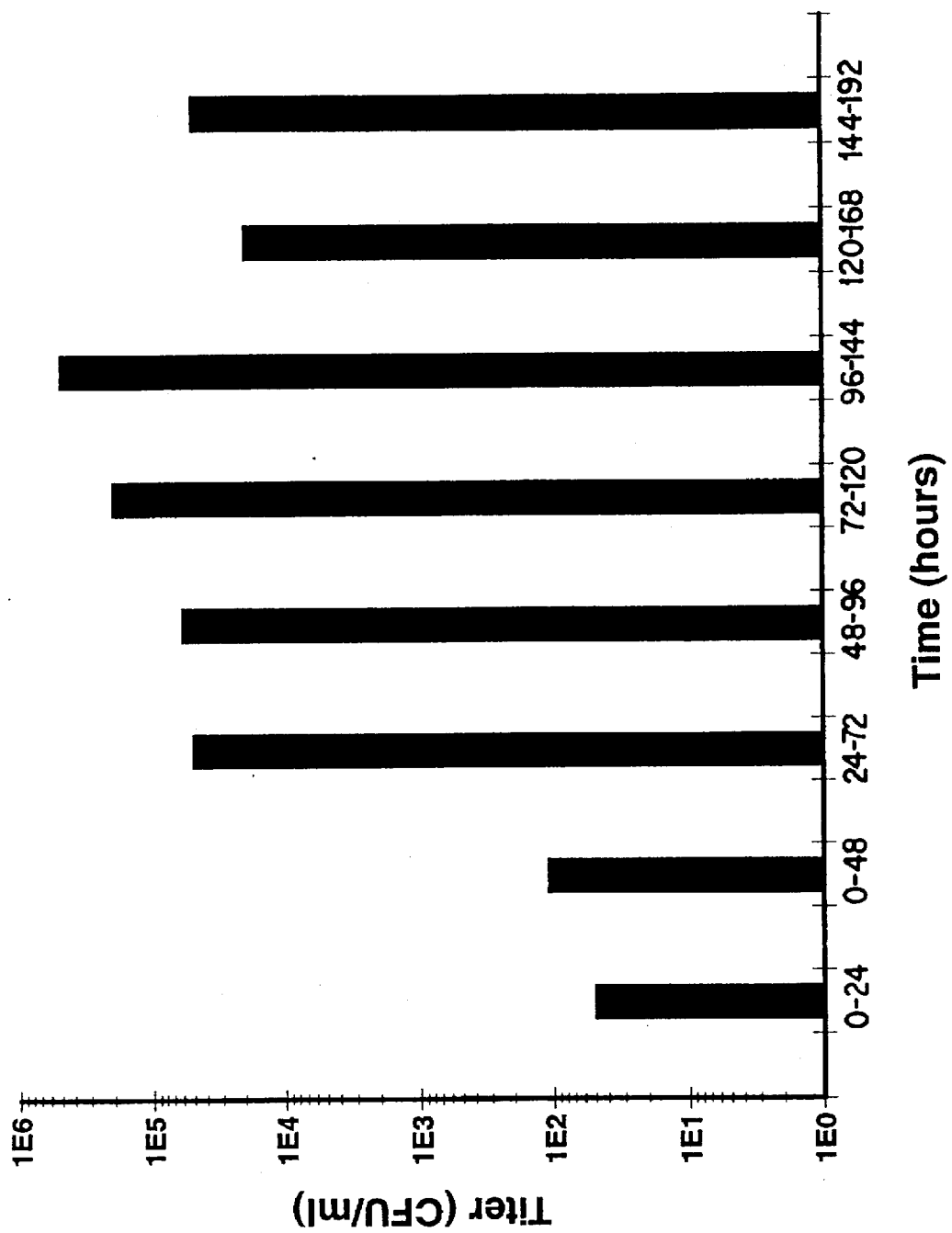
Figure 7A:
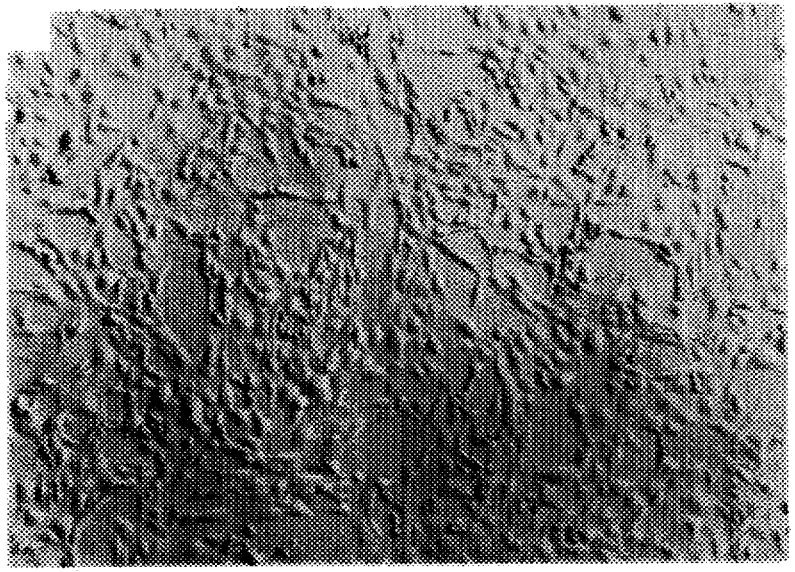
Figure 7B:
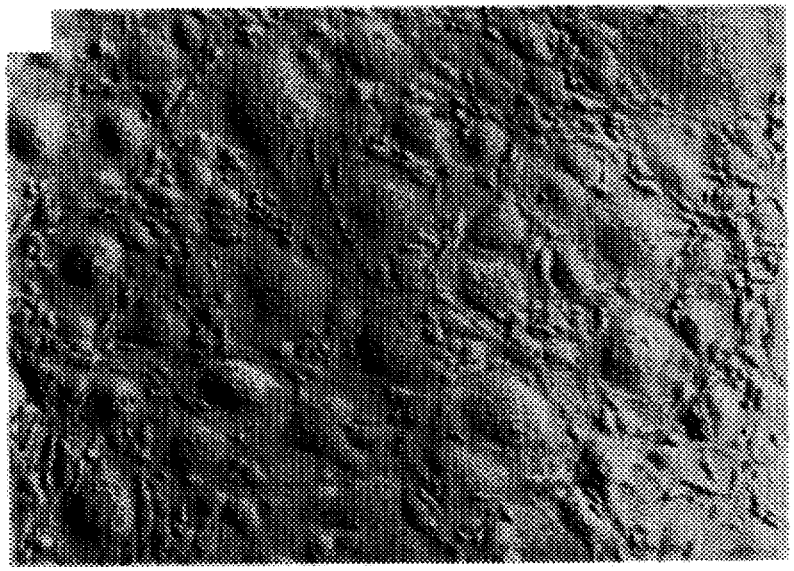

Following removal of tetracycline, the titer of infectious neo$^R$ CFU rose rapidly to more than 10$^5$/ml in media conditioned for 48 hours between 72 and 144 hours by clone GP7CN-tTA-G4 (FIG. 6). Despite massive syncytial formation by 72–96 hours (FIG. 7) and detachment of many cells by 120 hours, virus production continued at substantial levels as documented up to 192 hours. This virus could be concentrated more than 200-fold by ultracentrifugation with recovery of 50–100 percent of the infectious neo$^R$ particles (Table II). Concentrations of 10$^8$–10$^9$ CFU have been achieved.

Discussion

The data establish the feasibility of using the tetracycline-mediated system to obtain large quantities of MuLV vector particles pseudotyped with VSV-G envelope proteins. Evidence was obtained establishing that 3T3 cells are able to produce vector particles containing the GAG and POL components of MuLV with VSV-G as the predominant or exclusive membrane protein.

Thus, initial data were obtained by transient expression of VSV-G in derivatives of 3T3 cells. The later data show the derivation of a stable producer clone that inducibly expresses the VSV-G protein. A clone was obtained that constitutively expresses the tet$^R$/VP 16 chimeric transactivator and contains an integrated expression cassette in which the VSV-G coding sequences are under control of the tet$^O$ minimal promoter. These cells grow normally in the presence of tetracycline; after its removal, substantial amounts of VSV-G protein are expressed and large quantities of pseudotyped vector particles are released into the culture media.

Assembly and release of viral particles is thought to require the localized collection of transmembrane proteins that attract pre-formed nucleocapsid components through interaction of the C-terminal, internal domain of the envelope protein with matrix proteins (Stephens & Compans, Ann Rev. Microbiol. 42:489–516 (1988)). This model is supported by experimental data with respect to the assembly of native VSV particles (Whitt et al., J. Virol. 63:3569–3578 (1989)). The mechanism and site(s) of interaction of the VSV-G proteins with MuLV matrix proteins remains obscure. The data herein and previously published results (Burns, J. C. et al., Proc. Natl. Acad. Sci. (USA) 90:8033–8037 (1993); Yee, J. K. et al., Proc. Natl. Acad. Sci (USA) 91:9564–9568 (1994)) establish that such interactions are of adequate efficiency to support release of infectious viral particles at a rate that approximates that observed for native MuLV particles. Concentration of such pseudotyped vector particles has been routinely achieved by ultracentrifugation (Burns, J. C. et al., Proc. Natl. Acad. Sci. (USA) 90:8033–8037 (1993); Yee, J. K. et al., Proc. Natl. Acad. Sci (USA) 91:9564–9568 (1994); Table II). Application of this methodology to derive vector preparations for clinical applications is thus feasible.

The host range of VSV-G pseudotyped MuLV particles is greater than that of native MuLV. VSV is thought to utilize a ubiquitously distributed phospholipid as its receptor (Mastromarino, P. et al., J. Gen. Virol. 68:2359–2369 (1987)) and, despite its ability to induce intercellular syncytial formation (FIGS. 2 and 7), to enter cells by an endosomal pathway that depends on vesicular acidification (Marsh & Helenius, Adv. Virus Res. 36:107–151 (1989)).

It has been established that pseudotyped MuLV infect hamster, insect, frog and fish cell lines (Burns, J. C. et al., Proc. Natl. Acad. Sci. (USA) 90:8033–8037 (1993)) and exhibit higher infectivity, as reflected by apparent titer compared to standard amphotropic vector preparations, when tested on human tracheal epithelial cells (9HTEO), uterine cervical epithelial cells (HeLa) or primary human fibroblasts (Yee, J. K. et al., Proc. Natl. Acad. Sci (USA) 91:9564–9568 (1994)). Primary mouse hepatocytes are also efficiently infected by VSV-G (Yee, J. K. et al., Proc. Natl. Acad. Sci (USA) 91:9564–9568 (1994)). The Applicants have established (Table III) that NIH3T3, K562, and IM-9 cells are efficiently infected by VSV-G.

EXAMPLE 2

The cell line described above, GP-7CN-tetVP16-G (deposited as ATCC CRL-11875), produces retroviral particles in which the genome is G1Na while the envelope protein is VSV-G. This cell line was made by first infecting GP7C with the retrovirus G1Na to produce GP7CN. Subsequently, the plasmid expressing the VSV-G envelope protein was introduced.

GP-7CN-tetVP16-G already has a G1Na proviral integrant and thus can only produce retroviral particles which have G1Na as the genome. Since this cell line already has a proviral integrant, it is not feasible to introduce a second provirus since the resultant cell line would actually produce two different retroviral particles and would be unsuitable for gene therapy use. A more useful cell line is one in which a retroviral genome of choice could be introduced into the cell line. In this way a variety of retroviral vectors could be made, each of which would have the VSV-G protein as the envelope.

GP-7C-tetVP16, a cell line that expresses the tet/VP16 transactivator (tTA), was made by the calcium-phosphate mediated cotransfection of GP-7C with pUHD15-1 (a plasmid which contains the tTA gene under the control of the human cytomegalovirus promoter IE, Gossen and Bujard, Proc. Natl. Acad. Sci. USA 89:5547–5551 (1992)) and pUHD-puro2 (a plasmid in which the expression of the puromycin resistance gene is controlled by the tTA-dependent promoter) in the presence of puromycin. The resulting clones were analyzed for expression of tTA by first testing their resistance to puromycin in the presence and absence of tetracycline. Those clones which were resistant to puromycin in the absence of tetracycline but were puromycin sensitive in the presence of tetracycline were then analyzed by transient transfections with ptet$^O$-LacZ.

GP-7C-tetVP16-G, a cell line which expresses tTA and is capable of expressing the VSV-G protein in a tetracycline-dependent manner was made by cotransfecting GP-7C-tetVP16 with pUHD10-G and pTK5-109 in the presence of tetracycline and HAT. The resulting cell line, GP-7C-tetVP16-G, expressing tTA and tetracycline regulatable VSV-G gene, is a packaging cell line which can be used to produce a variety of retroviral vectors in which the envelope is the VSV-G protein.

A second method for producing the VSV-G packaging cell line, GP-7C-tetVP16-G, is by calcium phosphate-mediated cotransfection of GP-7C with pUHD-tet/VP16 puro (a plasmid in which the tTA gene is controlled by the tet$^O$-CMV minimal promoter and also contains the puromycin gene under the control of the PGK (phosphoglycerokinase promoter)), a gift from Dr. Dario Vignali, St. Jude Children's Research Hospital, and pUHD10-G (a plasmid in which the expression of the VSV-G gene is controlled by the tet$^O$-CMV minimal promoter) in the presence of tetracycline. The resultant clones were then tested for the ability of the cells to form syncytia in the absence of tetracycline. Those clones which formed substantial syncytia were then analyzed by Western blotting using an antibody specific for the VSV-G protein. The cell line expressing the highest levels of VSV-G protein was chosen as the VSV-G packaging cell line.

The Applicants have thus made a packaging cell line in which the expression of the VSV-G protein is under the control of tTA. This provides the ability to make retroviral producer cells lines with a number of different retroviral vectors incorporating a heterologous gene of choice for use in gene therapy technology. These retroviral producer cell lines have improved host range and can produce a high titer of retroviral vectors.

TABLE I

Neutralization of VSV-G Pseudotyped MuLV Vector Particles with Anti-VSV Antibodies

| Virus | Titer (cfu/ml)* | Pre-Immune Serum 1:100 | Pre-Immune Serum 1:10 | Anti-VSV Serum 1:100 | Anti-VSV Serum 1:10 |
|---|---|---|---|---|---|
| Pseudotyped G1Na | $1.2 \times 10^5$ | $1.3 \times 10^5$ | $8 \times 10^4$ | $3 \times 10^4$ | 0 |
| Wild Type VSV | $2.8 \times 10^8$ | N.T. | $4.3 \times 10^8$ | N.T. | $<10^4$ |
| Amphotropic G1Na | $6.0 \times 10^6$ | N.T. | $1 \times 10^6$ | N.T. | $8 \times 10^6$ |

*The amphotropic and VSV-G pseudotyped virus were determined on NIH3T3 cells, the wild type VSV was determined on L cells; N.T., not tested.

TABLE II

Concentration of VSV-G Pseudotyped MuLV Vector Produced by GP7CN-tTA-G4 Cell Line

| Producer Cell Line | Time of Induction (hrs) | Virus Titer (cfu/ml)* Pre-cen | Virus Titer (cfu/ml)* Post-cen | Fold Concentration | Total Virus (cfu) Pre-cen | Total Virus (cfu) Post-cen | % Virus Recovery |
|---|---|---|---|---|---|---|---|
| GP7CN.tTA-G4 | 72 | $2.8 \times 10^6$ | $3.0 \times 10^8$ | 230 | $5.4 \times 10^8$ | $2.6 \times 10^8$ | 48 |
| | 120 | $2.3 \times 10^7$ | $5.9 \times 10^9$ | 210 | $4.3 \times 10^9$ | $5.1 \times 10^9$ | 100 |
| | 168 | $6.6 \times 10^7$ | $6.1 \times 10^9$ | 190 | $12.2 \times 10^9$ | $6.3 \times 10^9$ | 52 |

*The virus titer was determined on NIH3T3 cells as described in methods.

TABLE III

Transduction of Human Cell Lines Using VSV-G Pseudotyped Retrovirions

| Virus | Titer (cfu/ml) NIH3T3 | K562* | CEM* | IM-9* |
|---|---|---|---|---|
| Amphotropic G1Na | $3 \times 10^6$ | $1.1 \times 10^4$ | $7 \times 10^3$ | $8 \times 10^3$ |
| VSV-G Pseudotyped G1Na (non-concentrated) | $2.0 \times 10^7$ | $4.5 \times 10^4$ | $2.5 \times 10^4$ | $1.3 \times 10^4$ |
| VSV-G Pseudotyped G1Na (concentrated) | $5 \times 10^9$ | $2.2 \times 10^6$ | $4.2 \times 10^5$ | $1.1 \times 10^5$ |

*CEM and K-562 are human leukemia cells and IM-9 is a human lymphoblast cell line.

What is claimed is:

1. A retrovirus packaging cell containing:
   (a) a first nucleic acid sequence, said sequence comprising a toxic viral envelope protein coding sequence operably linked to a minimal promoter, said minimal promoter being operably linked to at least one copy of the tetracycline operator, said sequence also comprising a sequence that stops transcriptional readthrough of the gene encoding said toxic viral envelope protein;
   (b) a second nucleic acid sequence, said sequence comprising a sequence encoding a chimeric protein, said chimeric protein comprising a tetracycline-modulated repressor and a transactivator protein, said chimeric protein coding sequence being operably linked to a promoter; and
   (c) a third nucleic acid sequence, said sequence comprising a sequence encoding retrovirus nucleocapsid protein.

2. The cell of claim 1, wherein said minimal promoter is the cytomegalovirus 1A minimal promoter.

3. The cell of claim 1, wherein said toxic viral envelope protein is the VSV-G protein.

4. The cell of claim 1, wherein said transactivator protein is the C-terminal activating region of the VP16 protein of HSV.

5. The cell of claim 1, wherein said minimal promoter is the cytomegalovirus 1A minimal promoter, said toxic viral envelope protein is the VSV-G protein, and said transactivator is the C-terminal activating region of the VP16 protein of HSV.

6. The cell of claim 5, designated GP-7C-tetVP16-G, deposited as ATCC CRL-11874.

7. A retrovirus producer cell containing:
   (a) a first nucleic acid sequence, said sequence comprising a toxic viral envelope protein coding sequence operably linked to a minimal promoter, said minimal promoter being operably linked to at least one copy of the tetracycline operator, said sequence also comprising a sequence that stops transcriptional readthrough of the gene encoding said toxic viral envelope protein;
   (b) a second nucleic acid sequence, said sequence comprising a sequence encoding a chimeric protein, said chimeric protein comprising a tetracycline-modulated repressor and a transactivator protein, said chimeric protein coding sequence being operably linked to a promoter;
   (c) a third nucleic acid sequence, said sequence comprising a sequence encoding retrovirus nucleocapsid protein; and
   (d) a fourth nucleic acid sequence, said sequence comprising a retroviral sequence capable of being encapsidated in said nucleocapsid protein.

8. The cell of claim 7, wherein said minimal promoter is the cytomegalovirus 1A minimal promoter.

9. The cell of claim 7, wherein said toxic viral envelope protein is the VSV-G protein.

10. The cell of claim 7, wherein said transactivator is the C-terminal activating region of the VP16 protein of HSV.

11. The cell of claim 7, wherein said minimal promoter is the cytomegalovirus 1A minimal promoter, said toxic viral envelope protein is the VSV-G protein, and said transactivator is the C-terminal activating region of the VP16 protein of HSV.

12. The cell of claim 7, wherein said retroviral sequence contains at least one heterologous gene that is capable of being expressed in a target cell.

13. The cell of claim 7, wherein said retrovirus is selected from the group consisting of Moloney murine leukemia virus and Harvey murine sarcoma virus.

14. A method for producing infectious retrovirus comprising incubating the cell of claim 7 in culture medium lacking tetracycline so that infectious retrovirus is produce from said cell.

15. A method for producing a retrovirus gene delivery vehicle comprising incubating the cell of claim 12 in cell culture medium lacking tetracycline so that retrovirus gene delivery vehicles are produced in said cell.

16. A retrovirus producer cell containing:

(a) a first nucleic acid sequence, said sequence comprising a toxic viral protein coding sequence operably linked to a minimal promoter, said minimal promoter being operably linked to at least one copy of the tetracycline operator, said sequence also comprising a sequence that stops transcriptional readthrough of the gene encoding said toxic viral envelope protein;

(b) a second nucleic acid sequence, said sequence comprising a sequence encoding a chimeric protein, said chimeric protein comprising a tetracycline-modulated repressor and a transactivator protein, said chimeric protein coding sequence being operably linked to a promoter; and (c) a third nucleic acid sequence, said sequence comprising a viral sequence sufficient to produce infectious virus in said cell, wherein production of said virus depends upon the expression of said toxic viral protein.

17. A nucleic acid sequence comprising the VSV-G coding sequence operably linked to a minimal promoter, said minimal promoter being operably linked to at least one copy of the tetracycline operator, said sequence also comprising a sequence that stops transcriptional readthrough of the gene encoding said toxic viral envelope protein.

18. The nucleic acid of claim 17, wherein said minimal promoter is the cytomegalovirus-1A minimal promoter.

19. A combination of nucleic acids comprising:

(a) a sequence encoding a toxic viral envelope protein, said sequence being operably linked to a minimal promoter, said minimal promoter being operably linked to at least one copy of the tetracycline operator, said sequence also comprising a sequence that stops transcriptional readthrough of the gene encoding said toxic viral envelope protein;

(b) a sequence encoding a chimeric protein, said chimeric protein comprising a tetracycline-modulated repressor and a transactivator protein, said chimeric protein coding sequence being operably linked to a promoter; and (c) a nucleic acid sequence encoding retrovirus nucleocapsid proteins.

20. The combination of claim 19, wherein said minimal promoter is a cytomegalovirus 1A minimal promoter.

21. The combination of claim 19, wherein said toxic viral envelope protein is the VSV-G protein.

22. The combination of claim 19, wherein said transactivator protein is the C-terminal activating region of the VP16 protein of HSV.

23. The combination of claim 19, wherein said minimal promoter is the cytomegalovirus 1A minimal promoter, said toxic envelope protein is the VSV-G protein, and said transactivator protein is the C-terminal activating region of the VP16 protein of HSV.

24. A combination of nucleic acids comprising:

(a) A sequence encoding VSV-G, said sequence being operably linked to a minimal promoter, said minimal promoter being operably linked to at least one copy of the tetracycline operator, said sequence also comprising a sequence that stops transcriptional readthrough of the gene encoding said toxic viral envelope protein; and (b) a sequence encoding a chimeric protein, said protein comprising the tetracycline-modulated repressor and a transactivator protein, wherein said chimeric protein coding sequence is operably linked to a promoter.

25. The combination of claim 24, wherein said minimal promoter is the cytomegalovirus 1A minimal promoter.

26. The combination of claim 24, wherein said transactivator protein is the C-terminal activating region of the VP16 protein of HSV.

27. The combination of claim 24, wherein said minimal promoter is the cytomegalovirus 1A minimal promoter and said transactivator protein is the C-terminal activating region of the VP16 protein of HSV.

* * * * *

UNITED STATES PATENT AND TRADEMARK OFFICE
CERTIFICATE OF CORRECTION

PATENT NO. : 5,750,396
DATED : May 12, 1998
INVENTOR(S) : Yanping Yang et al.

It is certified that error appears in the above-identified patent and that said Letters Patent is hereby corrected as shown below:

Column 1,
Line 2, please insert the following:
-- STATEMENT REGARDING FEDERALLY SPONSORED RESEARCH OR DEVELOPMENT
This invention was made with government support under NIH Grant No. CA 21765. The U.S. Government has certain rights in the invention. --

Signed and Sealed this

Twenty-first Day of June, 2005

JON W. DUDAS
*Director of the United States Patent and Trademark Office*